(12) United States Patent
Tedesco (10) Patent No.: US 7,153,132 B2
(45) Date of Patent: Dec. 26, 2006

(54) MINI-DENTAL IMPLANT SURGICAL STENT

(76) Inventor: James L. Tedesco, 7 Winterhall Rd., Orchard Park, NY (US) 14127

( * ) Notice: Subject to any disclaimer, the term of this patent is extended or adjusted under 35 U.S.C. 154(b) by 0 days.

(21) Appl. No.: 11/174,706

(22) Filed: Jul. 5, 2005

(65) Prior Publication Data

US 2006/0263743 A1    Nov. 23, 2006

Related U.S. Application Data (60) Provisional application No. 60/594,971, filed on May 23, 2005.

(51) Int. Cl.
*A61C 3/02* (2006.01)
(52) U.S. Cl. ........................................ 433/76
(58) Field of Classification Search ................ 433/72, 433/74, 76, 172, 173
See application file for complete search history.

(56) References Cited

U.S. PATENT DOCUMENTS

| | | |
|---|---|---|
| 4,260,383 A | 4/1981 | Weissman |
| 5,133,660 A | 7/1992 | Fenick |
| 5,320,529 A | 6/1994 | Pompa |
| 5,350,297 A | 9/1994 | Cohen |
| 5,556,278 A | 9/1996 | Meitner |
| 5,613,852 A | 3/1997 | Bavitz |
| 5,630,717 A | 5/1997 | Zuest et al. |
| 5,725,376 A | 3/1998 | Poirier |
| 5,915,962 A | 6/1999 | Rosenlicht |
| 5,927,982 A | 7/1999 | Kruger |
| 5,967,777 A | 10/1999 | Klein et al. |
| 6,296,483 B1 | 10/2001 | Champleboux |
| 6,382,975 B1 | 5/2002 | Poirier |
| 6,626,667 B1 | 9/2003 | Sussman |
| 6,672,870 B1 | 1/2004 | Knapp |
| 6,814,575 B1 | 11/2004 | Poirier |
| 6,869,282 B1 | 3/2005 | Carmichael et al. |
| 6,869,283 B1 | 3/2005 | Sussman |
| 2002/0102517 A1 | 8/2002 | Poirier |
| 2002/0137003 A1 | 9/2002 | Knapp |
| 2003/0134252 A1 | 7/2003 | Sussman |
| 2003/0157457 A1 | 8/2003 | Blacklock |
| 2003/0165791 A1 | 9/2003 | Carmichael |
| 2004/0013999 A1 | 1/2004 | Sussman |
| 2004/0048225 A1 | 3/2004 | Fletcher |
| 2004/0219480 A1 | 11/2004 | Malin |
| 2004/0234922 A1 | 11/2004 | Schuman et al. |
| 2005/0037320 A1 | 2/2005 | Poirier |

OTHER PUBLICATIONS

Winter, Alan A., D.D.S., et al. 'Cone Beam Volumetric Tomography vs. Medical CT Scanners NYSDJ, Jun./Jul. 2005, p. 28-32.

*Primary Examiner*—Cary E. O'Connor
(74) *Attorney, Agent, or Firm*—James J. Ralabate (57) ABSTRACT

A stent used to drill a pilot hole for dental implants is the subject of this invention. The stent has a base plate with drill directional cylinders fixed in this base plate. These cylinders are positioned so that they will reach the bone structure of a patient prior to and during the drilling of the pilot hole in the patient's jawbone.

10 Claims, 6 Drawing Sheets

MINI-DENTAL IMPLANT SURGICAL STENT

CROSS REFERENCES TO RELATED APPLICATIONS

This application claims the benefit of U.S. Provisional Application No. 60/594,971 filed May 23, 2005.

BACKGROUND OF THE INVENTION

This invention relates to a dental stent and more specifically to a sub-gingival tissue, bone supported, mini-dental implant surgical stent and method of using same.

It is known to use dental implants to replace missing teeth in a patent's mouth using various procedures. Dental implant procedures generally involve drilling a pilot hole into the jaw bone of a patient and inserting an implant into the hole provided. The crown is then cemented to the top section of the implant to complete the procedure. There are various prior art stents used as drill guides for drilling the initial pilot hole. These prior art procedures usually require the purchase of high-tech, very expensive apparatus. The pilot hole in an implant procedure is critical since it provides the hole into which the implant will be based and must be drilled along an acceptable path to insure maximum strength to the eventual implant. The larger mini-implant surgical stents in use today are fabricated with thick vacuum formed plastic that covers the biting surfaces of many teeth adjacent to the surgical site. These stents, by virtue of their size and thickness above the teeth, drastically reduce access to the surgical site, especially in the posterior molar regions where the tongue and cheek muscles already reside making multiple instrumentation procedures exceedingly difficult, if possible at all.

In addition to the large stent, a directional device with a three inch long handle is required to help direct the pilot drill. Not only does it restrict vision even further, the long "lever" easily torques the stent right or left and is difficult to hold steady when the surgeon has to hold the drill at the proper angle with one hand, hold the directional device's handle with the other, keep the stent down without twisting it left or right, all the while fighting the tongue and cheek muscles from throwing the bone drill off line. A water syringe and suction tip are thrown into the mix, reducing vision further. It is almost impossible in these prior art procedures to see if the pilot drill is entering at the right spot or at the right angle. Getting four or five mini implants into their proper positions and at a 90 degree angle to the biting surfaces of the adjacent teeth often becomes a nightmare for the surgeon and patient alike. These are the experiences several dentists have had that convinced the present inventor to find a better way. Other prior art surgical stents require expensive computer imaging, 3D CT scans, and/or computer assisted digital x-ray images, as integral to stent fabrication. Time consuming and expensive systems such as these are the sort of items that have kept implant dentistry out of financial reach of the average patient and are contrary to the mission of the mini-implant dentistry, which is to bring the benefits of implant dentistry to other than the very wealthy patients. Prior art stents do not (nor is it their intention) provide the accuracy necessary to cement a permanent crown the same day as the surgery; the present invention can accomplish this.

The simplicity of the present bone supported surgical stent in both design and function, as well as its low cost, offer a remarkable unique solution for the accurate placement of implants and immediate placement of teeth (crowns).

Several prior implant guides and procedures are known such as those described in U.S. Pat. Nos. 4,260,383; 5,133,660; 5,320,529; 5,350,297; 5,556,278; 5,613,852; 5,630,717; 5,725,376; 5,915,962; 5,927,982; 5,967,777; 6,296,483; 6,382,975; 6,626,667; 6,672,870; 6,814,575; 6,869,282 and 6,869,283. In all of these patents, terms, materials, procedures and technical terminology are used which will form a foundation for known technical terms and disclosures that may be used in describing portions of the present invention.

SUMMARY OF THE INVENTION

In the present invention, a novel low cost implant stent or drill guide is used to accurately guide a drill needed for the critical initial pilot hole.

It is therefore an object of this invention to provide a novel, efficient and improved implant stent devoid of any above noted and other disadvantages of prior art stents.

Another object of this invention is to provide a dental stent that solves the difficult heretofore alignment problems that frequently arise when drilling the pilot hole or holes and permits a very high success rate in implant procedures.

Still a further object of this invention is to provide a simply constructed dental stent uniquely adapted for use in implant procedures including mini-dental implant procedures.

Yet another object of this invention is to provide a stent that eliminates or minimizes any lateral movement of said stent or the guide cylinders fixed in the base plate of the stent.

Another still further object of this invention is to provide a guide cylinder(s) that will extend down to and touch the patient's jaw bone and thereby provide maximum drill guidance.

A still further object of this invention is to provide a dental stent that can materially shorten the implant procedure, and one that does not require the usual prior art high technical skills of the dental surgeon or dentist.

Other objects will become apparent upon a reading of this disclosure.

The above objects and others are accomplished by providing the following stent: The dental surgical stent of this invention comprises a base plate having a defined length, width and height. A tube-like cylinder(s) is located and fixed in the base plate and at least one of these open tube-like cylinder projects vertically through the thickness or height of the base plate. This open cylinder extends beyond the lower thickness portion of the base plate and is constructed to reach and contact the patient's jaw bone, thereby providing a drill guide for the drill that fits into the immovably fixed cylinder all the way down to the bone structure. This arrangement ensures a pilot hole that will be drilled exactly where it needs to be, and in multiple pilot holes where they will be substantially parallel to each other. Looking down at a top plan view of the stent, these cylinders can be in alignment or can be staggered. Thus, to obtain by the present invention a precise pilot hole exactly where intended:

a) the stent and base plate must fit tightly between adjacent teeth (adjacent to the implant site) so no lateral movement is permitted;

b) the placement cylinder must have a length equal to the sum of the thickness of the base plate, plus the thickness of the tissue up to the bone, or equal to the distance from the bottom base plate to the top bone structure; this is critical to the present invention, and c) the drill used to create the pilot hole must have a diameter that will tightly but movably fit into the placement cylinder, and be of a length beyond the length of said cylinder; and d) as earlier noted, the open cylinder tubes are of a length sufficient to rest on or contact the jaw bone of a patient just before and during the drilling.

Perhaps the most compelling idea in the hearts and minds of dentists and oral surgeons everywhere is the ability to give patients with missing teeth permanent, esthetically pleasing teeth, sometimes in only one surgical appointment or minimal appointments. Some dentists have tried to reach this minimal appointment goal but few have succeeded in all areas of the mouth. Other implant prior art placement systems allowed dentists to place implants during the first surgical appointment. Unfortunately, in this prior art procedure more appointments are necessary, over a long period of time, while waiting for healing, before a permanent crown can be placed.

The new surgical protocol: After the patient is anesthetized, the present surgical stent is placed between the teeth with the cylinders resting on the tissue. Firm pressure is applied into the tissue, the stent is removed, and the pressure points created on the tissue are examined. A tissue punch or a round nose diamond high-speed drill that approximates the diameter of the cylinders is used to remove the tissue down to the bone with irrigation. The stent is placed, each cylinder going into its respective hole until it is fully seated. The cylinders and matrix material resting on the ridge provide sufficient support and resistance from movement so that the bone drill is guided into the precise spot intended, without the need for additional directional devices currently used that aren't always successful and are cumbersome when used in the molar regions, often resulting in stretched patient's lips and post-operative discomfort. The pilot holes are drilled to the length desired by inserting a bone drill through each cylinder. The cylinders are irrigated before and during this step. The sub-gingival stent is removed and the mini implants are placed in the pilot holes and turned down according to the known IMTEC (IMTEC is a trademark of Imtec Corporation) mini implant placement protocol. This protocol generally involves removing implant from its sealed tube by plastic handle and place quickly into pilot hole. Start turning into pilot hole. After resistance is encountered, remove plastic handle and replace with metal hand driver. Turn slowly and when resistance is encountered, change to thumb wench. It is also recommended by this point that a 15 second rest period follow each turn to allow for bone expansion. X rays should be taken at 2 or 3 intervals during placement to check implant's progress. A hand wrench (ratchet) is used for the final few millimeters, for rock solid seating of implant. A torque wrench may also be used. A stent with a large cylinder may be used at this point to help guide the implant to position.

The Mini-Dental Bone-Supported Implant Placement (MDI) stent of this invention provides a safe, sure and almost foolproof system for inserting implants accurately. The present system is so efficient and accurate that even the average clinician will be able to place MDI's (define MDI) in all regions of the mouth, including the second molar region. This fact will allow many more dentists and clinicians to feel confident and succeed in multiple MDI placements (long span fixed bridge work). This invention will improve the status and success of MDI fixed crown and bridge applications throughout the international dental community.

This invention as earlier noted relates to a mini-dental implant surgical stent that provides an accurate and precise guide for the bone drill when making a pilot hole for MDI placement surgery; obviously, it can be used in other than in mini procedures. That is, standard implants having dimensions greater than mini implants and that are "immediate load" implants. The invention consists of two main components: Depth and guide cylinders and stent matrix material of base plate. The cylinders have an internal diameter that are just slightly larger than the corresponding bone drill's exterior diameter. The drill tracks precisely and provides great resistance from going off line. The stent material or base plate is made of materials offered to the dental market and is used to hold the cylinders in their position during pilot hole drilling. This invention also involves a new surgical protocol in addition to the Sub-Gingival Bone Supported MDI Surgical Stent. Any suitable substantially non-toxic base plate material and cylinder material may be used both known and to be used in the future.

After a crown is fabricated by the lab (any suitable lab protocol can be used in the present invention), the working model including the lab implant analog and crown or bridge is examined for quality, contacts and occlusion. Next, the technician or stent fabricator will pull the analogs out of the working model and place and fix metal cylinders in the holes that are revealed after the analogs are removed. The depth the cylinder(s) are placed is determined by close examination of Bite-Wing x-rays taken at a 90 degree angle. The distance in millimeters is measured from the crest of bone to the gingival surface at the position of the implant. The cylinder is placed and fixed into the working model at the corresponding depth. Once all cylinders are placed in their respective holes, a resin stent material (or other accepted stent matrix material) is placed over the cylinders and, in one embodiment, lapping the ridge about 8 mms on either side. There is no need to cover the teeth on either side of the implant site or space as the sub-gingival cylinders provide sufficient stabilization when drilling pilot holes. This is particularly important when placing teeth that have open space posteriorly. Since the cylinders exactly match the angle of the Analog and end directly on the bone, the pilot hole is always precise with the bone drill tracking through the cylinder into the bone at the proper spot and angle substantially undeterred by knife edges or extremely dense areas of bone.

Most of the implant placement failures and near failures in the prior art involve a bone knife edge on the posterior ridge. Starting a pilot hole, as in the prior art, with a drill guide which is 3, 4, 5, or 6 mm away from the dense bone of a knife edge is a very difficult proposition. A high speed round bur does not always help. If the round bur, that starts the pilot hole, is off line by even 0.5 mm, the implant abutment will be angled so far out of position that the crown may not fit properly even with a long adjustment process. Using the present stent and drill guide cylinder, directly contacting the bone ridge eliminates this problem. The procedure is faster and less traumatic.

This also allows for a smaller crown cement cavity. The smaller cavity means a tighter, stronger fit to the implant. Film thickness of the cement is greatly reduced allowing firmer cementing to the implant abutment, and less overflow of cement into the space between the gingival tissue and crown that must be removed after cementing with some appreciable effort.

Although the present placement stent was developed with mini-implants (generally less than 3 mm in diameter) protocols in mind, new developments in immediate load standard implant design (more than 3 mm in diameter) and placement protocols will allow the present stent to be effective with larger implants as well. It merely requires the use of multiple cylinders, one inside the other matching the larger bone drills used during sequential osteotomies. Using the stent and procedure of the present invention, a dental impression is taken by the dentist, a lab working model is made either in a dental lab or by some other means. As earlier noted, any suitable steps may be taken by the dentists before they send their case to a lab; also, any suitable steps a lab technician performs when he or she gets the case may be used with the present invention. A lab analog is made in the working model. A porcelain crown is fabricated to lab analog. The stent of this invention is fabricated using the lab model with the analog removed. The length of the cylinder or cylinders of this invention is determined after an evaluation of gingival tissue depth by a perioprobe having horizontal markings to indicate the depth. The stent with the cylinders in place is placed between adjacent teeth and pressure applied to the stent causes the cylinders to mark a cylindrical circular mark on the tissue. The tissue at this cylinder marking is removed down to the patient's bone. The stent is then placed with the cylinders reaching unobstructively to the bone. A drill is placed into the open cylinders for guidance down to the bone and the pilot hole drilled in the bone guided by the cylinder(s).

A second placement stent with a wider cylinder is used when seating the implant structure into the pilot hole of the bone. When the implant is set in the final position, a permanent crown is cemented to the abutment atop the implant. Throughout the entire procedure careful sterile conditions are followed to prevent any infection.

Throughout this specification and claims, "cylinders" will be used; however only one cylinder may also be used.

It must be remembered that in order to cement a permanent crown the same day the implant is placed, precise and accurate placement of the implant is necessary. The clinician, dentist or oral surgeon must insert the implant exactly where the analog is in the working lab stone model. The present placement stent provides this accuracy and will get the job done. Obviously, suitable surgical infection control protocols are maintained throughout the fabrication and surgical phases.

DETAILED DISCUSSION OF DRAWINGS AND PREFERRED EMBODIMENTS

Figure 1:
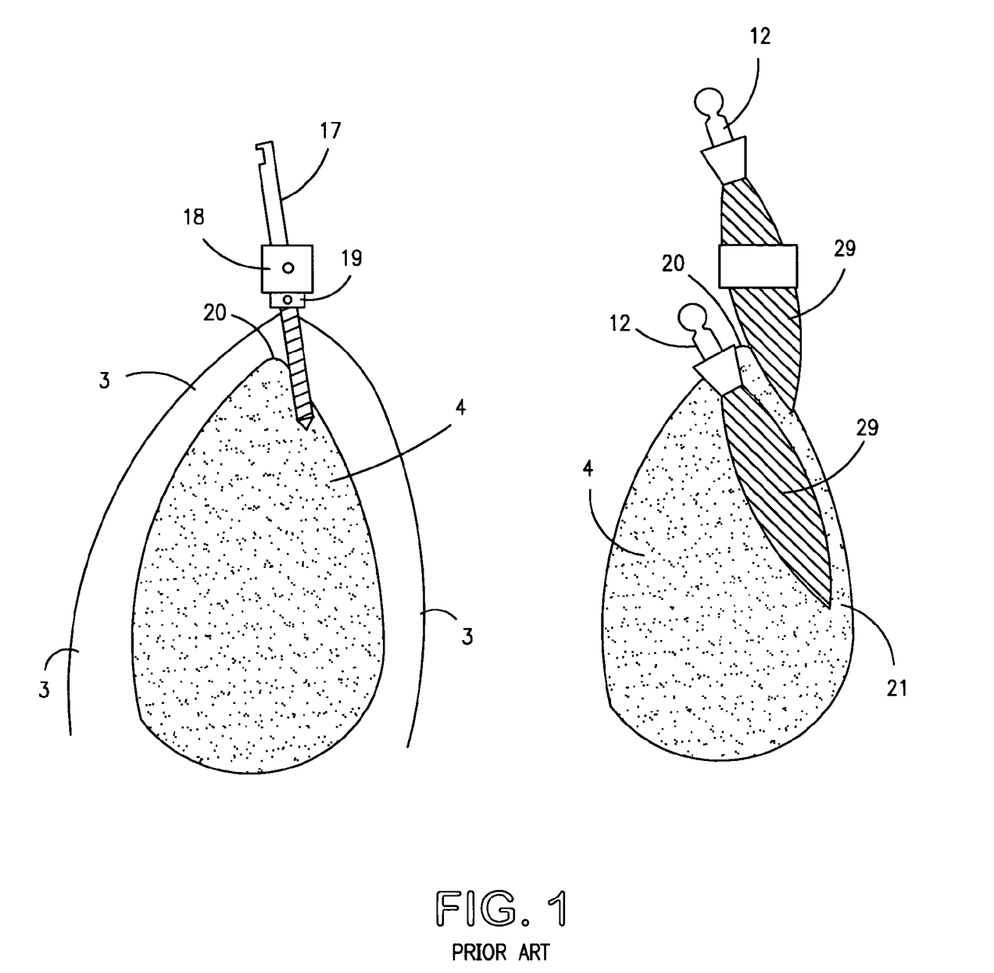
FIG. 1 is a perspective view of the prior art stent and an illustration of potential problems.
Figure 2:
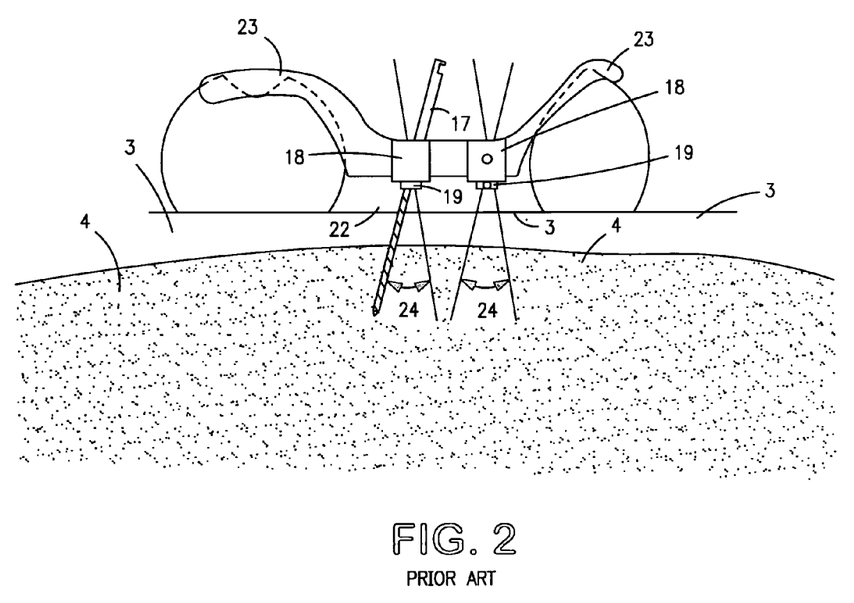
FIG. 2 is another perspective view of the prior art stent and an illustration of how problems can occur.

In FIGS. 1 and 2, the prior art stent is illustrated. In the prior art stents 23 and accompanying procedures, the bone drill 17 has too much play due to the large distance between the drill guide 18 and the bone 4. The guide 18 and directional device 19 stops atop the patient's tissue 3 and must travel generally from 2 to 6 mm distance 22 before it contacts the bone 4. If the pilot drill 17 can't engage the bone's knife edge 20, it will slide down the buccal plate 21 of the bone, chewing up attached gingiva. The result is an implant body 29 or abutment 12 out of position and at an angle to the long axis of the ridge. This implant body 29 may also be dangerously close to the buccal plate 21.

In FIG. 2, a side view of the prior art stent 23 having placement ring 18 and directional device 19 is shown where the directional device 19 stops above the patient's gum tissue 3. The bone drill 17 may have too much play and usually moves the somewhat large distance shown at 24, therefore the excessive play in prior art drill guides 18 and drill guide directional devices 19 allow for easy misplacement of the pilot hole. An object of the present invention, as earlier noted, is to provide a novel stent devoid of these prior art disadvantages.

Figure 3:
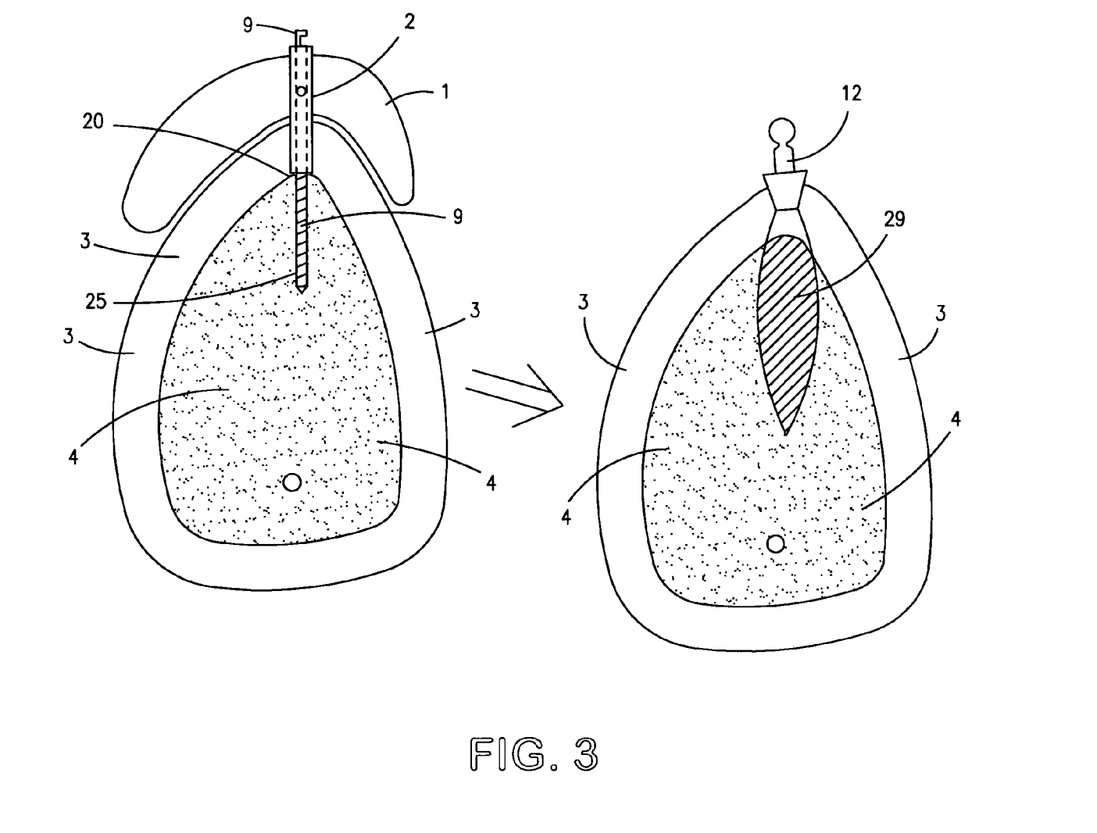
FIG. 3 is a perspective view of the stent of this invention when in place and in use with the bone drill.

In FIG. 3 a plan view of the stent 1 of this invention is illustrated. Stent 1 having a base plate 28 contains a placement cylinder(s) tube 2 that guides the drill 9 right up to a point atop the knife edge 20 of the patient's bone 4. Any number of cylinders 2, one or more may be used. The curvature of stent 1 which fits around gum tissue 3, and the deep penetrating placement cylinder 2 through dense, attached gingival tissue (up to bone) to provide a very secure, substantially immovable guide for drill 9 resulting in a very precise and accurate pilot hole 25. The thickness of tissue 3 (usually about 2 to 4 mm) is penetrated by placement cylinder 2 up to the knife edge 20 of the bone 4. The bone drill 9 exits the directional placement cylinder 2 exactly at the desired location on the bone 4. The cylinder's 2 long length prevents the bone pilot drill 9 from going off line. The result is an exposed abutment 12 and implant body 29 that is in proper position and parallel to the long axis of the ridge.

The prior art devices and protocol do not come close to providing the accuracy needed to cement the permanent crown 13 the same day as abutment 12 and implant body 29 placement; on a consistent basis. Generally, as earlier noted, unlike the present invention, in the prior art, the thick dense bone edge 20 throws the bone drill far off line either left or right, thus preventing proper alignment of abutment 12.

Figure 4:
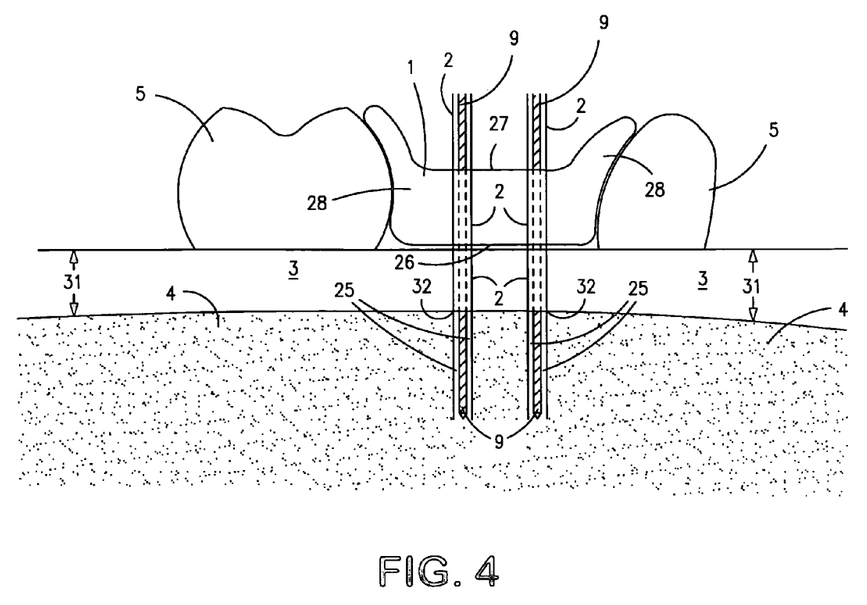
FIG. 4 is a plan view of the stent of this invention when in place between the patient's teeth prior to and during drilling.

In FIG. 4, the seating of the stent 1 of this invention comprising a base plate 28 and cylinders 2 is shown where placement cylinder(s) 2 are fixed therein the bottom portion of base plate 28 abuts against the top of gingival tissue 3 and the base plate sides fit tightly against the adjacent teeth 5. Notice that the length of open or tubular cylinders 2 extends openly from the top 27 of base plate 28 to the top of bone structure 4. Cylinders 2 extend from the top 27 of base plate 28 (in stent 1) through the base plate 28, beyond the lower portion 26 of the base plate 28, and extends through the gingival tissue 3 and ending when in use when they touch the bone structure 4 at location 32. As noted earlier, the drill 9 creates pilot holes 25 exactly where they need to be and substantially parallel to each other.

Figure 6A:
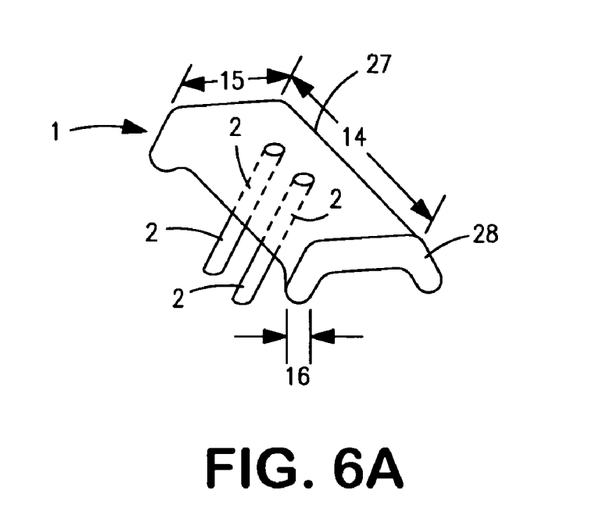
FIG. 6(a) is a top perspective view of the stent of this invention, with the cylinders aligned and showing the length, width and thickness of the stent.
Figure 7:
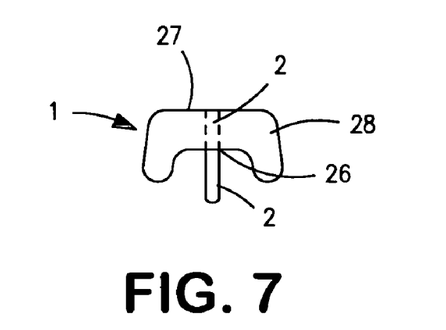
FIG. 7 is a side plan view of an embodiment of the stent of this invention.

In FIG. 4, cylinders 2 are shown for clarity in the drawings as extending in their upper portions substantially beyond the upper surface 27 of base plate 28. Generally, however, the open cylinders 2 can be flush or even with surface 27 as shown in FIGS. 6A and 7. However, it is within the scope of this invention for cylinders 2 to be flush as in FIG. 7 or they can extend beyond surface 27 as shown in FIG. 4.

Figure 5:
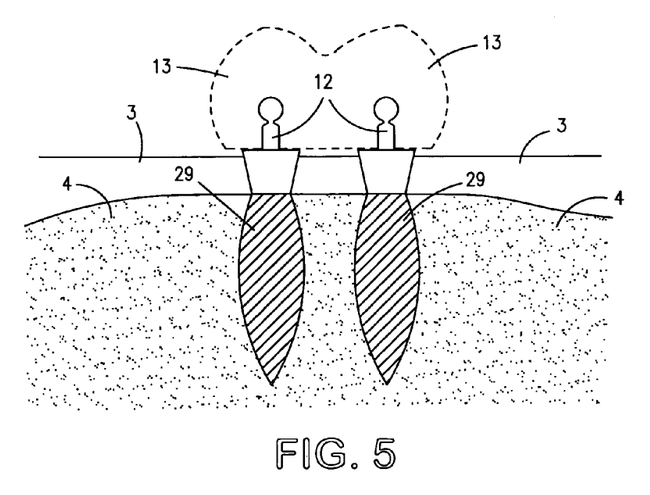
FIG. 5 is a plan view of the abutments in place and the crown cemented thereon in the procedure of this invention.

In FIG. 5 as a result of use of our stent 1, the abutments 29 end up in perfect position, parallel to each other for easy cementation of the pre-fabricated crown 13. Known crown and bridge abutment 29 may be used in the present invention or any other suitable abutment may be used.

Figure 6B:
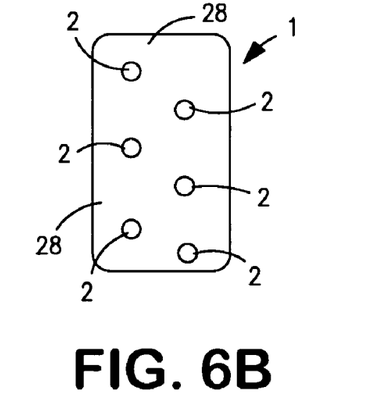
FIG. 6(b) is a top plan view of and embodiment of the stent of this invention showing the staggered placement of the cylinders.

In FIG. 6(a) a top perspective of the stent 1 of this invention is illustrated comprising a base plate 28 and cylinders 2 fixed therein. Note that the stent 1 is three dimensional having a length 14, a width 15, and a thickness (or height) 16. The base plate 28 is made from any suitable plastic non-toxic material such as a standard dental acrylic or others including silicone-based materials or vacuum-formed stent materials. The cylinders 2 can be made from any suitable non-toxic materials, metal or plastic such as stainless steel, metal alloys, or any other suitable materials. The cylinders 2 may be staggered, as the preferred embodiment shown in FIG. 6(b) rather than being aligned as in the embodiment shown in FIG. 6(a) of the drawings. Aligning multiple posterior MDI's when replacing 2–4 teeth in a staggered manner (rather than a straight line, as shown in FIG. 6(a) provides additional support from buccal lingual forces. This advantage allows for the fabrication of wider (buccal-lingual) crowns, for increased chewing power (a larger occlusal table) and more natural looking teeth. FIG. 6(b) shows in a top stent view the stent 1 with preferred staggered arrangement protocol.

FIG. 7 is a side plan view of the stent 1 of the present invention. Note that drill guides or cylinder(s) 2 extend beyond the lower portion 26 of base plate 28.

Figure 8:
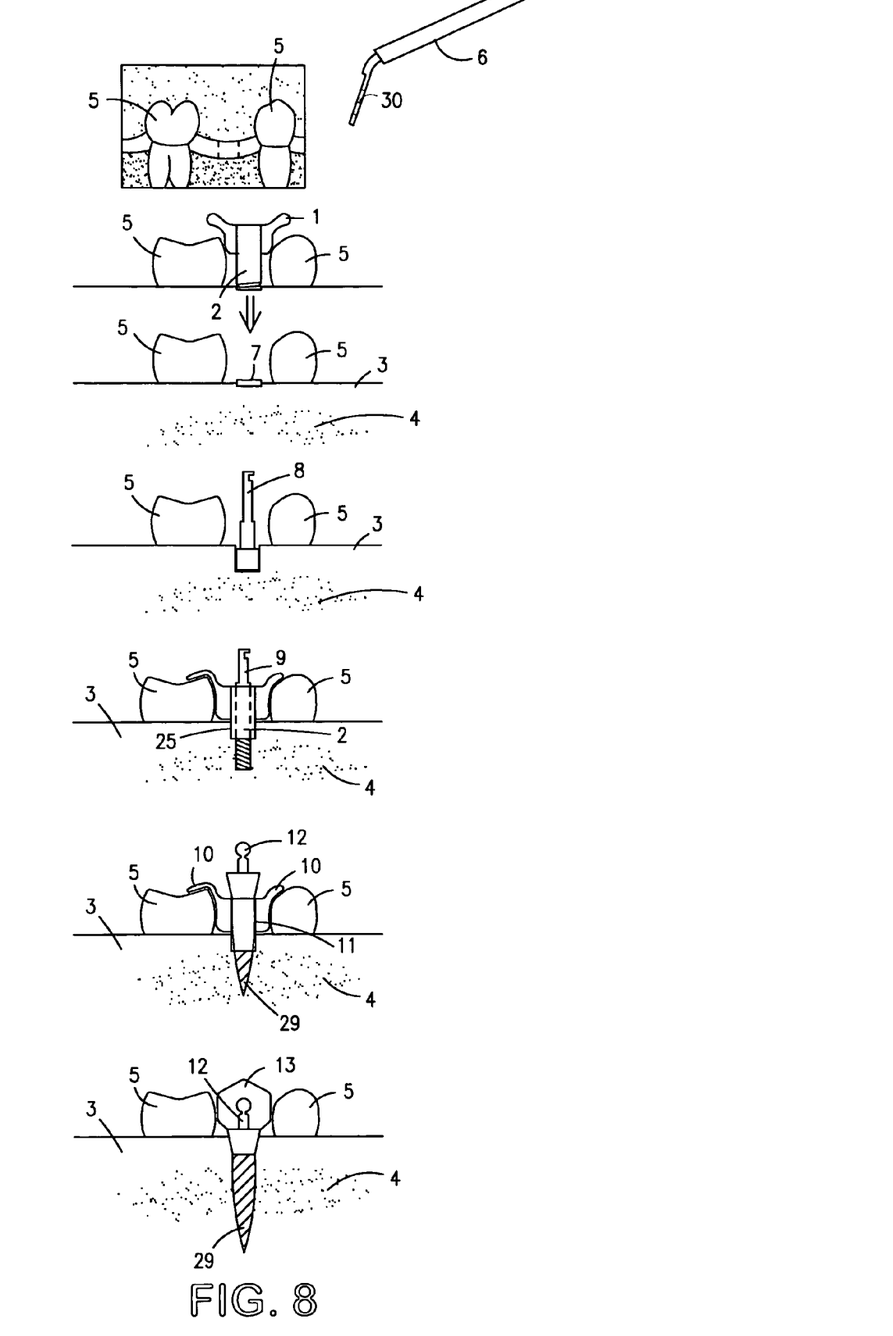
FIG. 8 is a sequential step by step plan view of the use of the stent and method of this invention up to the final placement of the implant and crown.

In FIG. 8, the sequence of steps of the preferred embodiment of this invention are illustrated. The general procedure is initially followed, i.e., once the dental impression is taken by the dental surgeon, a lab working model is made with a lab analog in position. A final porcelain crown is fabricated to lab analog. A bone supported placement stent is fabricated using the lab model with the analog removed. Then the length or depth of the placement cylinder 2 of this invention is determined by bite wing x-rays and evaluation of gingival tissue depth 31 with perioprobe 6 having horizontal markings 30. Then the stent 1 of this invention is placed over ridge and adjacent teeth 5 of patient. Pressure is applied to stent 1 creating a circle marking 7 caused by the contact of tube or cylinder 2 with the tissue 3 of the patient. A standard tissue punch 8 or diamond burr or other suitable means is used to remove the small amount of tissue 3 down to the bone 4. The stent 1 is placed to full depth-placement cylinder 2 resting on crest of bone 4. A pilot hole 25 is made by drill 9 exactly where it needs to be in bone 4 and at proper angle. Obviously, every patient will be different so that the stent 1 and tube's 2 length, etc. must be determined for each patient. Subsequently a second placement stent 10 with a wider cylinder 11 is used when seating the implant body 29 in the bone 4. The stent 10 is then removed, the implant 29 is set to final position and a permanent crown 13 is cemented to abutment 12.

The only way a pre-made, final and permanent crown can be cemented (on an abutment and an implant) the same day is when the margin of the implant 29 ends up in the same position as the margin of the lab analog on the working model.

An added benefit of this stent is the cylinders' ability to bring sterile water directly to the bone/bone drill interface, to keep the bone from heating and burning, which increases the chances for implant failure. All pilot drills are too small for internal irrigation channels; therefore all implants which require only one bone drill will immediately benefit from the stent of this invention. The tight interface between firm attached gingival (gum) tissue and the shaft of the pilot drill prevents much irrigation from reaching the bone/bone drill interface. The surgical handpieces have external irrigation, but the path to the bone/bone drill interface is further blocked by the large size of the prior art stents and is also encumbered by the directional devices' coverage of the surgical site.

The preferred and optimally preferred embodiments of the present invention have been described herein and shown in the accompanying drawings to illustrate the underlying principles of the invention, but it is to be understood that numerous modifications and ramifications may be made without departing from the spirit and scope of this invention.

What is claimed is:

1. A dental surgical stent useful for providing a drill guide when making a pilot hole for an implant procedure, said stent comprising a base plate and at least one tube-like cylinder, said base plate having a length whereby its longitudinal terminal portions fit tightly between teeth adjacent an area of the intended implant, said base plate enabled thereby to provide substantially no base plate lateral movement, said cylinder(s) being rigidly fixed in said base plate and are substantially immovably positioned therein, said cylinder(s) extending downwardly beyond the thickness of said base plate, said cylinder extending to a point where it is enabled to contact and rest upon the jawbone of the patient when in use prior to setting the implant.

2. The stent of claim 1 wherein said base plate has a lower surface which provides a structural form to mate with and fit substantially tightly against and abuts the upper gum tissue of a patient.

3. The stent of claim 1 whereby said cylinder(s) is a guide means into which a drill is securely but movably positioned when making a pilot hole for placement of the implant.

4. The stent of claim 1 whereby said cylinder(s) has a length at least equal to the thickness of said base plate plus beyond the thickness of the patient's tissue and enabled to contact and rest upon said jawbone.

5. The stent of claim 1 where the length of said cylinder(s) is predetermined for each patient in a manner so that said length is sufficient for said cylinder to contact said jawbone of a patient when forming a pilot hole for said implant.

6. The stent of claim 1 wherein said cylinder(s) are positioned in said base plate in a staggered fashion.

7. The stent of claim 1 wherein said base plate on its longitudinal terminal portions fits tightly against adjacent teeth, on its lateral sections it encircles a portion of the upper gum, and has the cylinder(s) projecting beyond its lower thickness portion enabled to contact and rest upon said jawbone during a pilot hole drilling.

8. A method to be used in a pilot hole drilling for a dental implant procedure which comprises providing a stent comprising a base plate having open drill guide cylinders rigidly fixed therein, and extending down to a bone structure, placing said stent between teeth adjacent an area of the intended implant, applying pressure to said stent and cylinders to cause cylinder marks on a patient's tissue, removing said stent and removing said tissue (cylinder marked) down to the patient's jawbone, replacing and wedging said base plate and cylinders in said area so as to provide substantially no base plate lateral movement, said cylinders enabled to reach rigidly and unobstructively to the bone, placing a drill into the open cylinders to provide thereby drill guidance down to the bone, and subsequently drilling a pilot hole in said bone prior to placing an implant body and abutment in said pilot hole.

9. The method of claim 8 wherein said stent is provided which fits substantially tightly against teeth adjacent the area of the intended implant.

10. The method of claim 8 wherein said tissue is removed prior to seating said stent for drilling said pilot hole.

* * * * *